United States Patent
Kelly

(10) Patent No.: US 11,090,189 B2
(45) Date of Patent: Aug. 17, 2021

(54) EYE DROP ALIGNMENT ASSEMBLY

(71) Applicant: Earl Kelly, Nashville, TN (US)

(72) Inventor: Earl Kelly, Nashville, TN (US)

( * ) Notice: Subject to any disclaimer, the term of this patent is extended or adjusted under 35 U.S.C. 154(b) by 266 days.

(21) Appl. No.: 16/268,914

(22) Filed: Feb. 6, 2019

(65) Prior Publication Data
US 2020/0246185 A1  Aug. 6, 2020

(51) Int. Cl.
*A61F 9/00* (2006.01)

(52) U.S. Cl.
CPC .................. *A61F 9/0026* (2013.01)

(58) Field of Classification Search
CPC ... A61F 9/0026; A61F 9/0008; B65D 23/003; A61M 35/003; A61B 17/0231
USPC ........................................................ 604/302
See application file for complete search history.

(56) References Cited

U.S. PATENT DOCUMENTS

| 4,685,906 A | 8/1987 | Murphy |
| 4,960,407 A | 10/1990 | Cope |
| 5,578,020 A | 11/1996 | Mosley |
| 7,891,615 B2 * | 2/2011 | Bevirt ................... F16M 13/022 248/181.1 |
| 2009/0259204 A1 | 10/2009 | Galdeti |
| 2010/0286634 A1 | 11/2010 | Marx |
| 2019/0358083 A1 * | 11/2019 | Barash ................... A61F 9/0026 |

FOREIGN PATENT DOCUMENTS

| IL | 259550 | * | 5/2018 |
| KR | 20120060386 A | * | 6/2012 |
| KR | 20150069128 A | * | 6/2015 |

* cited by examiner

*Primary Examiner* — Nicholas J Weiss
*Assistant Examiner* — Seth Han

(57) ABSTRACT

An eye drop alignment assembly includes a ring that has a bottle of eye drops being extendable therethrough. The ring has a plurality of engagements thereon and the engagements are spaced apart from each other and are positioned at strategic points around the ring. A plurality of legs is each movably coupled to a respective one of the engagements. A plurality of extensions is each pivotally coupled to a respective one of the legs. Each of the extensions is positionable at a selected angle with respect to the respective leg for aligning with a respective top and bottom eyelid. Additionally, each of the extensions spaces the ring away from the eyeball associated with a top and bottom eyelids. In this way the ring aligns the bottle of eye drops with the eyeball for successfully dispensing eye drops onto the eyeball.

3 Claims, 6 Drawing Sheets

EYE DROP ALIGNMENT ASSEMBLY

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to alignment devices and more particularly pertains to a new alignment device for aligning a bottle of eye drops with an eyeball.

BRIEF SUMMARY OF THE INVENTION

An embodiment of the disclosure meets the needs presented above by generally comprising a ring that has a bottle of eye drops being extendable therethrough. The ring has a plurality of engagements thereon and the engagements are spaced apart from each other and are positioned at strategic points around the ring. A plurality of legs is each movably coupled to a respective one of the engagements. A plurality of extensions is each pivotally coupled to a respective one of the legs. Each of the extensions is positionable at a selected angle with respect to the respective leg for aligning with a respective top and bottom eyelid. Additionally, each of the extensions spaces the ring away from the eyeball associated with a top and bottom eyelids. In this way the ring aligns the bottle of eye drops with the eyeball for successfully dispensing eye drops onto the eyeball.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
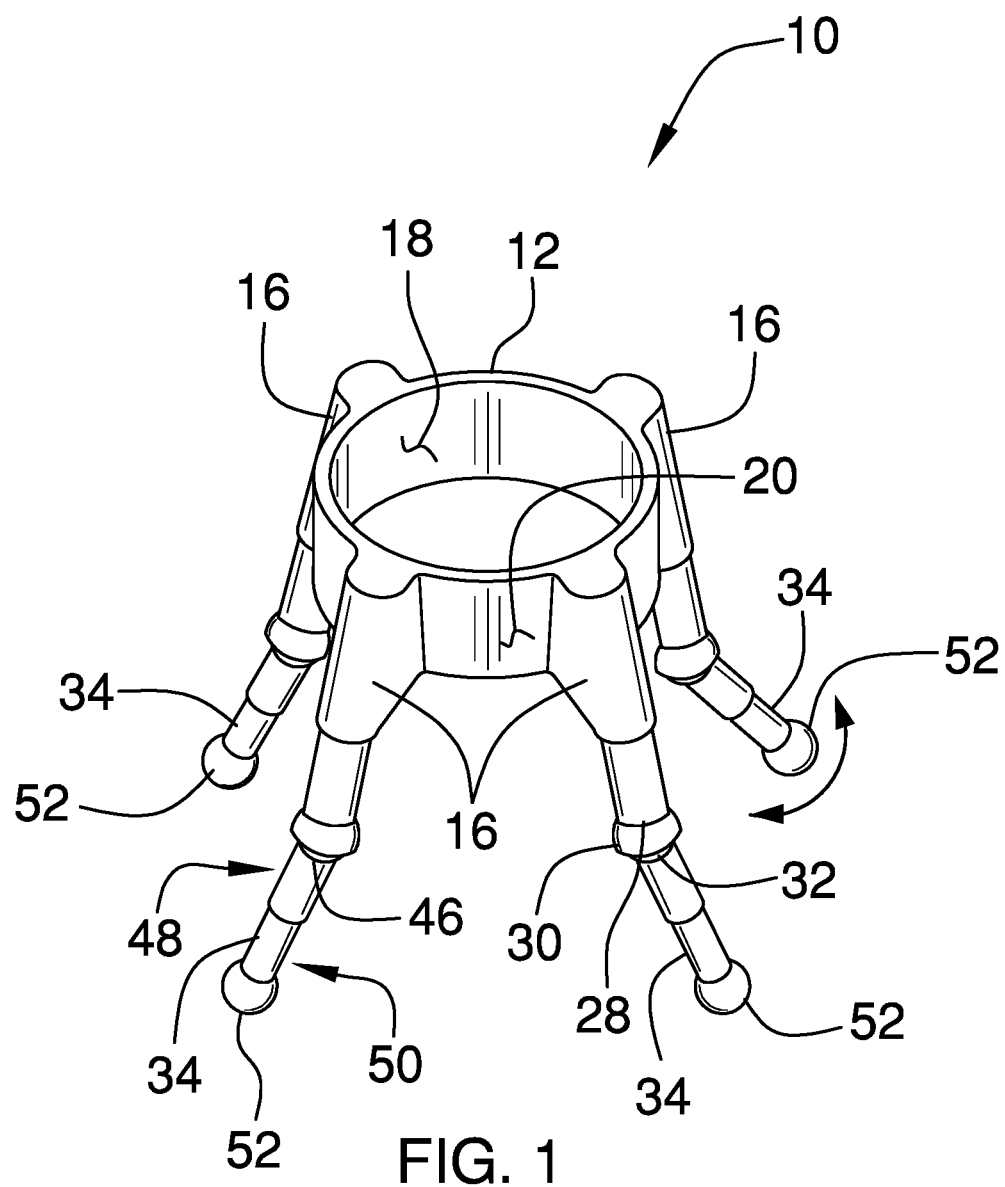
FIG. 1 is a top perspective view of an eye drop alignment assembly according to an embodiment of the disclosure.
Figure 2:
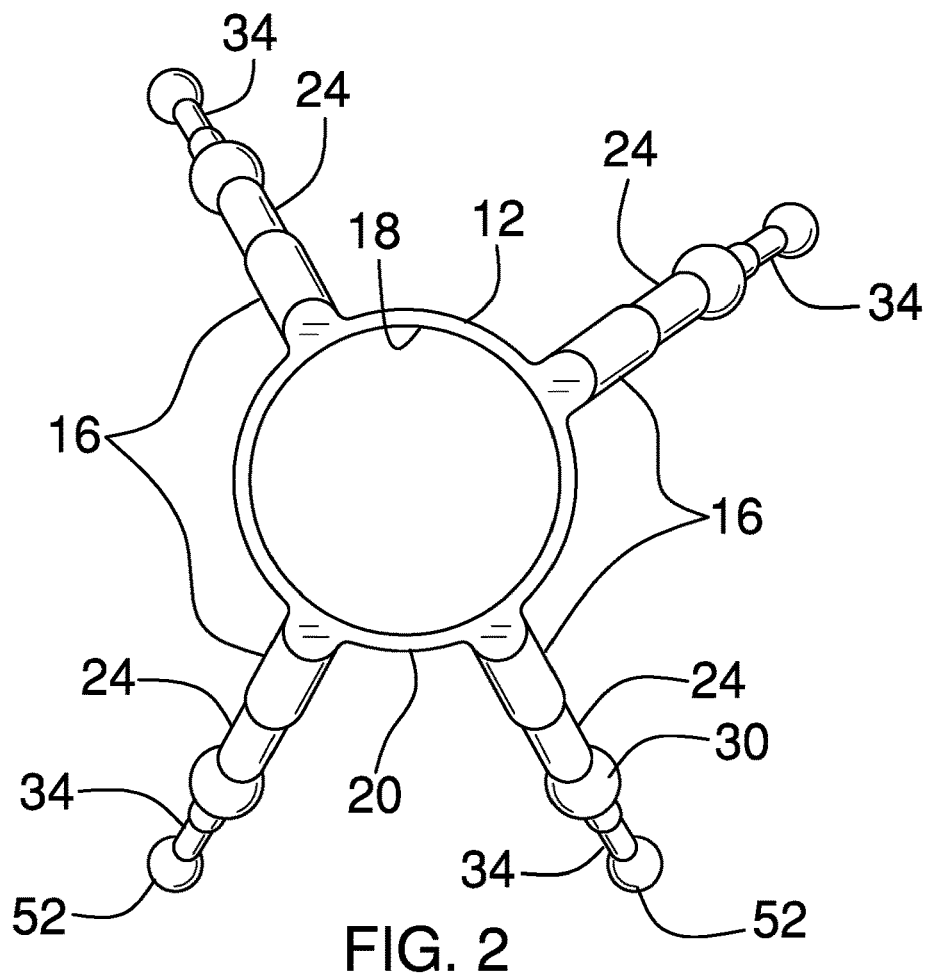
FIG. 2 is a top view of an embodiment of the disclosure.
Figure 3:
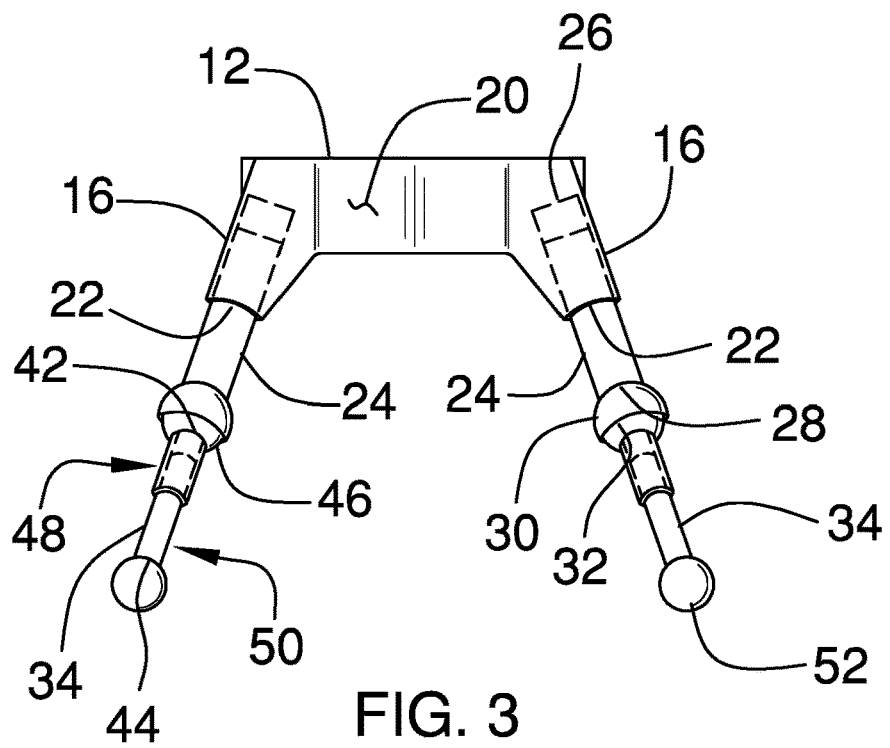
FIG. 3 is a front phantom view of an embodiment of the disclosure.
Figure 4:
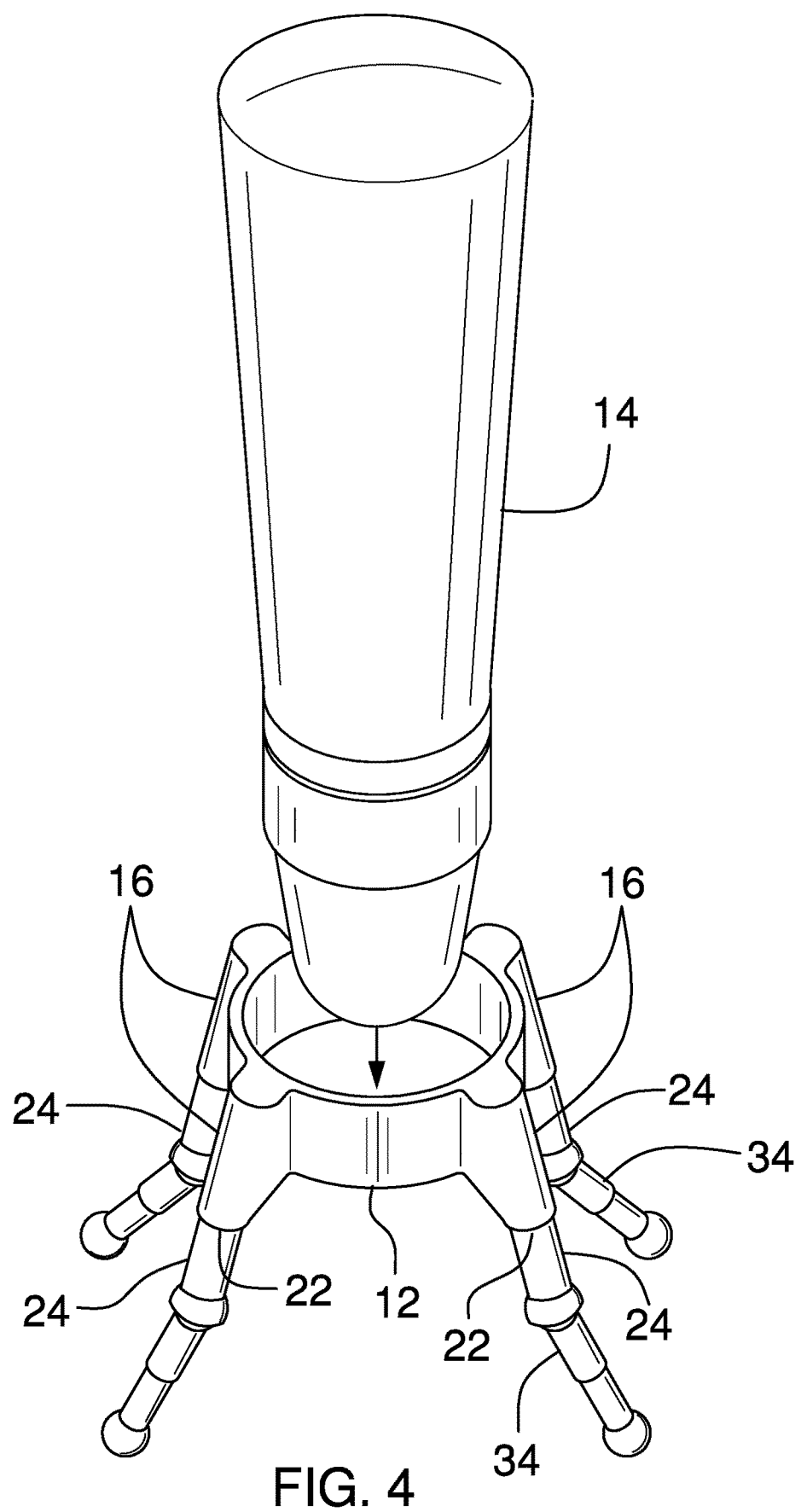
FIG. 4 is an exploded perspective view of an embodiment of the disclosure showing an eye drop bottle being inserted into a ring.
Figure 5:
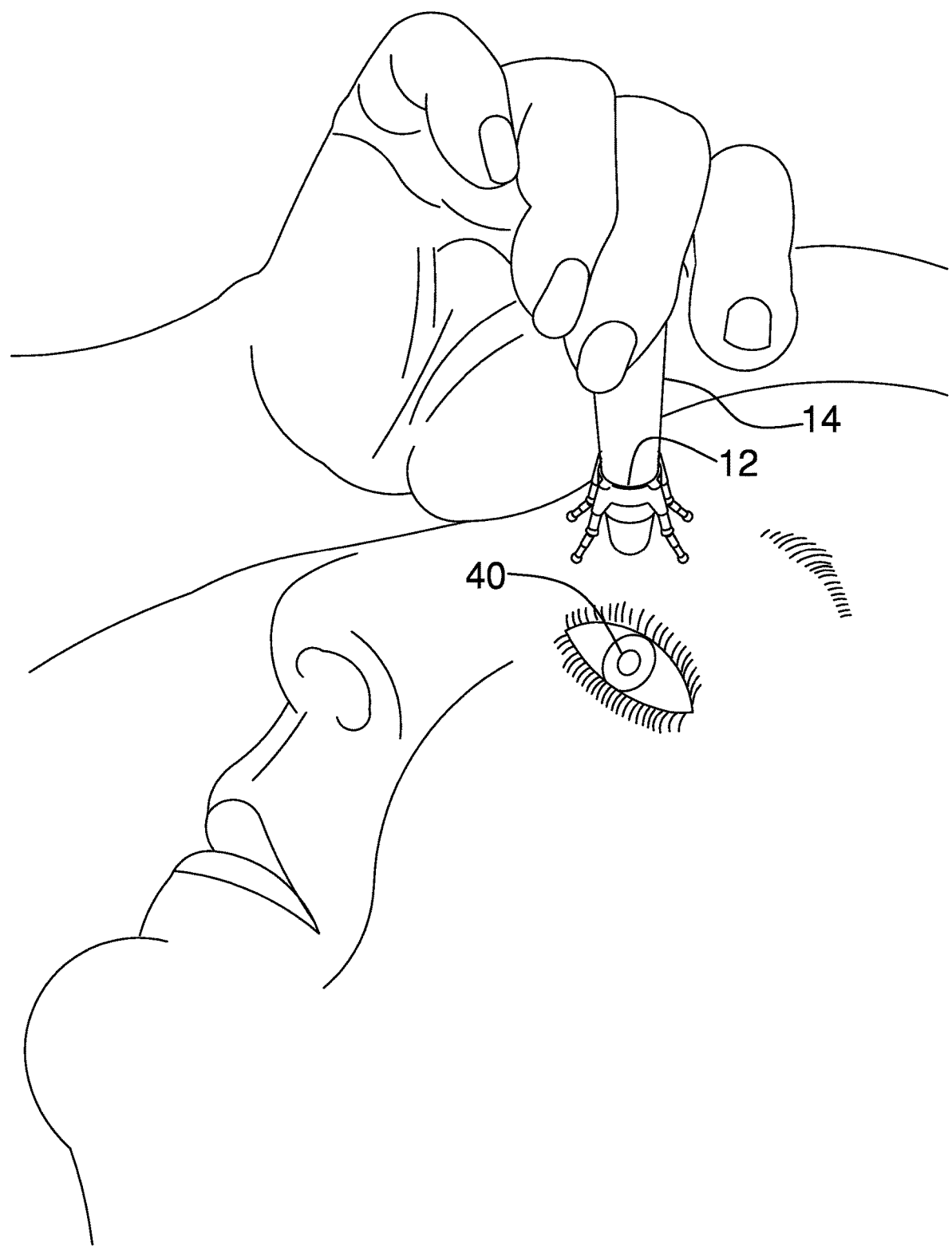
FIG. 5 is a perspective in-use view of an embodiment of the disclosure.
Figure 6:
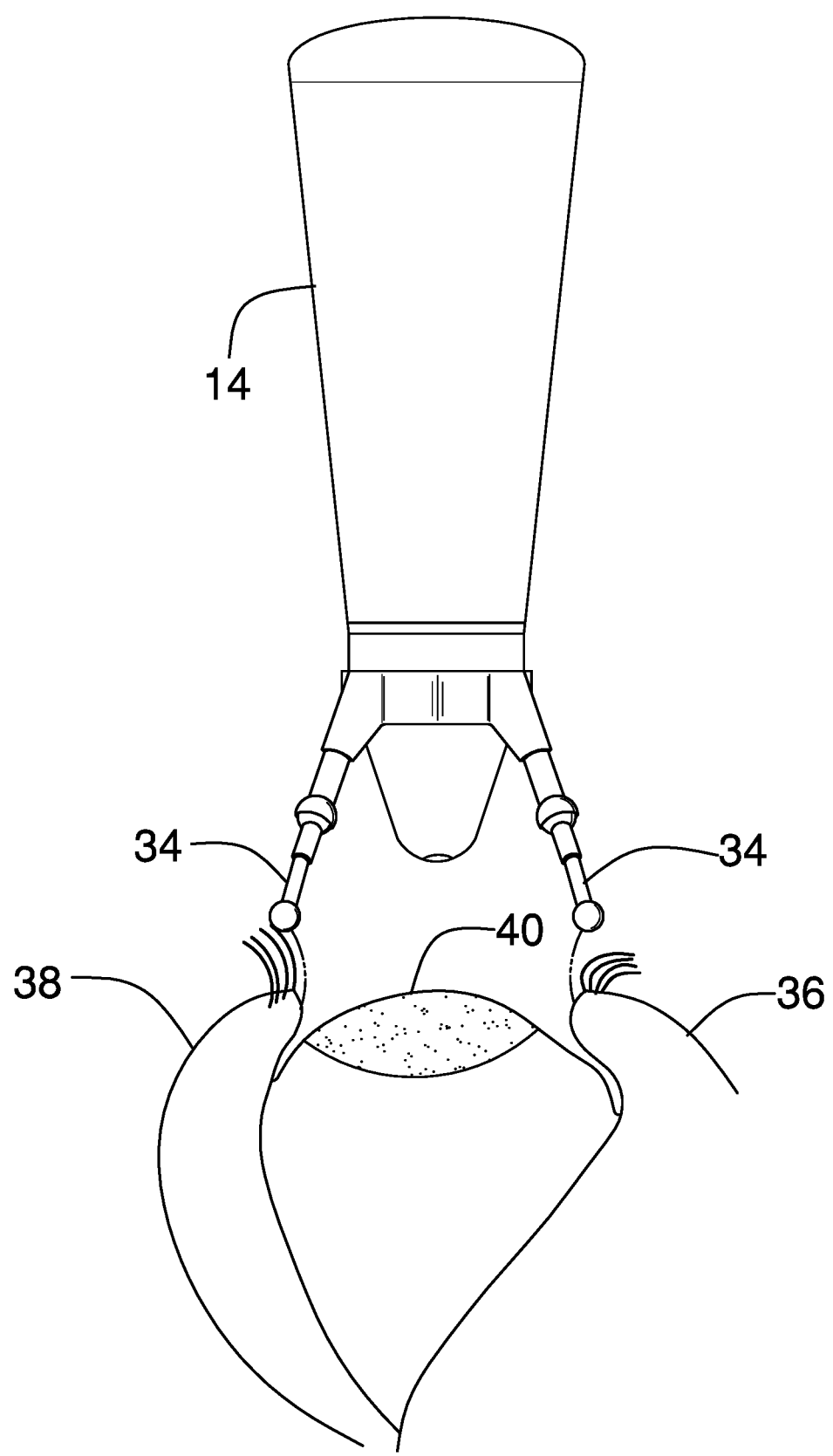
FIG. 6 is a perspective view of an embodiment of the disclosure being aligned with a respective top and bottom eyelid.
Figure 7:
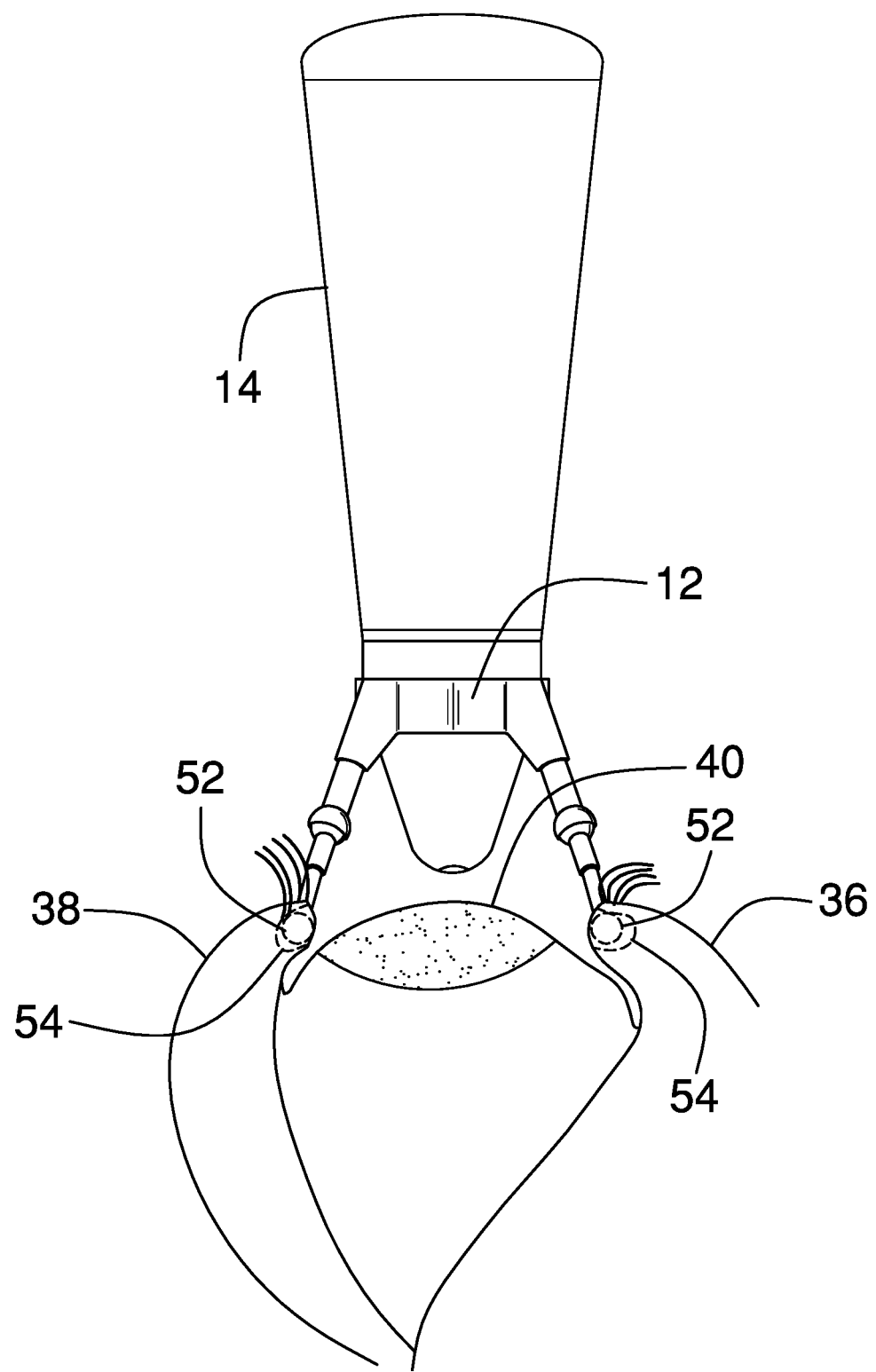
FIG. 7 is a perspective view of an embodiment of the disclosure showing mounting balls engaging a conjunctiva sac in a top and bottom eyelid.

With reference now to the drawings, and in particular to FIGS. 1 through 7 thereof, a new alignment device embodying the principles and concepts of an embodiment of the disclosure and generally designated by the reference numeral 10 will be described.

As best illustrated in FIGS. 1 through 7, the eye drop alignment assembly 10 generally comprises a ring 12 that can have a bottle of eye drops 14 extended therethrough. The bottle of eye drops 14 may be over the counter eye drops or prescription eye drops. The ring 12 has a plurality of engagements 16 thereon and the engagements 16 are spaced apart from each other around the ring 12. Additionally, each of the engagements 16 is positioned at strategic points around the ring 12.

The ring 12 has an inner surface 18 and an outer surface 20. Each of the engagements 16 is positioned on the outer surface 20 and the inner surface 18 engages the bottle of eye drops 14. Each of the engagements 16 has a bottom end 22 and the bottom end 22 of each of the engagements 16 is open. The strategic points of the engagements 16 may include the eleven o'clock position, the two o'clock position, the five o'clock position and the seven o'clock position with respect to the ring 12. Additionally, each of the engagements 16 angles outwardly away from the outer surface 20 of the ring 12.

A plurality of legs 24 is each of the legs 24 is movably coupled to a respective one of the engagements 16. Each of the legs 24 has a first end 26 and a second end 28, and the first end 26 of each of the legs 24 is inserted into the bottom end 22 of the respective engagement 16. The second end 28 of each of the legs 24 has a cup 30 positioned thereon. Moreover, the cup 30 on the second end 28 of each of the legs 24 has an open end 32, and the open end 32 of each cup 30 is directed away from the leg 24 upon which each cup 30 is positioned.

A plurality of extensions 34 is each pivotally coupled to a respective one of the legs 24. Each of the extensions 34 is positionable at a selected angle with respect to the respective leg 24. In this way each of the extensions 34 can be aligned with a respective one of a top eyelid 36 and bottom eyelid 38. Each of the extensions 34 spaces the ring 12 away from the eyeball 40 associated with the top 36 and bottom 38 eyelids a distance ranging between approximately 1.0 inch and 1.5 inches. In this way the ring 12 can align the bottle of eye drops 14 with the eyeball 40 for successfully dispensing eye drops 14 onto the eyeball 40. Additionally, each of the extensions 34 may have a pivotal range of approximately 40.0 degrees with respect to a longitudinal axis of the respective leg 24.

Each of the extensions 34 has an upper end 42 and a lower end 44, and the upper end 42 of each of the extensions 34 has a coupling ball 46 thereon. The coupling ball 46 on the upper end 42 of each of the extensions 34 is rotatably positioned in the cup 30 on the second end 28 of the respective leg 24. In this way each of the extensions 34 is pivotally retained on the respective leg 24. Each of the extensions 34 is manipulated into the selected angle with respect to the ring 12 to facilitate the ring 12 to be centered around a pupil of the eyeball 40. Each of the extensions 34 comprises a first half 48 that slidably engages a second half 50 such that each of the extensions 34 has a telescopically adjustable length.

A plurality of mounting balls 52 is each coupled to a respective one of the extensions 34. Thus, each of the mounting balls 52 engages the conjunctiva sac 54 of a respective one of the top 36 and bottom 38 eyelids when the extensions 34 are aligned with the top 36 and bottom 38 eyelids. Each of the mounting balls 52 is comprised of a smooth material to inhibit irritating the conjunctiva sac 54. Additionally, each of the mounting balls 52 is comprised of a hypo-allergenic material to inhibit initiating an allergic response in the conjunctiva sac 54. Each of the mounting balls 52 is positioned on the lower end 44 of the respective extension 34.

In use, the extensions 34 are manipulated into the selected angle to facilitate each of the extensions 34 to be aligned with the respective top 36 and bottom 38 eyelids. Each of the mounting balls 52 is urged into the conjunctiva sac 54 on the respective top 36 and bottom 38 eyelids. In this way the ring 12 is spaced from the eyeball 40 and the ring 12 is centered on the eyeball 40. The bottle of eye drops 14 is positioned in the ring 12 thereby facilitating the bottle of eye drops 14 to successfully dispense eye drops 14 directly onto the eyeball 40. Each of the mounting balls 52 is removed from the conjunctiva sac 54 on the respective top 36 and bottom 38 eyelids when the eye drops 14 have been successfully dispensed onto the eyeball 40.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An eye drop alignment assembly being configured to engage the conjunctiva sac of an eyeball thereby facilitating a bottle of eye drops to be aligned with the eyeball, said assembly comprising:

a ring having a bottle of eye drops being extendable therethrough, said ring having a plurality of engagements thereon, said engagements being spaced apart from each other and being positioned at points around said ring;

a plurality of legs, each of said legs being movably coupled to a respective one of said engagements;

a plurality of extensions, each of said extensions being pivotally coupled to a respective one of said legs, each of said extensions being positionable at a selected angle with respect to said respective leg wherein each of said extensions is configured to be aligned with a respective one of a top eyelid and bottom eyelid, each of said extensions spacing said ring away from the eyeball associated with the top and bottom eyelids wherein said ring is configured to align the bottle of eye drops with the eyeball for successfully dispensing eye drops onto the eyeball;

a plurality of mounting balls, each of said mounting balls being coupled to a respective one of said extensions wherein each of said mounting balls is configured to engage the conjunctiva sac of a respective one of the top and bottom eyelids;

wherein said ring has an inner surface and an outer surface, each of said engagements being positioned on said outer surface, said inner surface engaging the bottle of eye drops, each of said engagements having a bottom end, said bottom end of each of said engagements being open;

wherein each of said legs has a first end and a second end, said first end of each of said legs being inserted into said bottom end of said respective engagement, said second end of each of said legs having a cup being positioned thereon, said cup having an open end, said open end being directed away from said leg upon which said cup is positioned;

wherein each of said extensions has an upper end and a lower end, said upper end of each of said extensions having a coupling ball thereon, said coupling ball on said upper end of each of said extensions being rotatably positioned in said cup on said second end of said respective leg thereby pivotally retaining each of said extensions on said respective leg; and wherein each of said extensions is manipulated into the selected angle with respect to said ring to facilitate said ring to be centered around a pupil of the eyeball, each of said extensions comprising a first half slidably engaging a second half such that each of said extensions has a telescopically adjustable length.

2. The assembly according to claim 1, wherein:

each of said mounting balls is comprised of a smooth material wherein each of said mounting balls is configured to inhibit irritating the conjunctiva sac;

each of said mounting balls is comprised of a hypo-allergenic material wherein each of said mounting balls is configured to inhibit initiating an allergic response in the conjunctiva sac; and each of said mounting balls is positioned on said lower end of said respective extension.

3. An eye drop alignment assembly being configured to engage the conjunctiva sac of an eyeball thereby facilitating a bottle of eye drops to be aligned with the eyeball, said assembly comprising:

a ring having a bottle of eye drops being extendable therethrough, said ring having a plurality of engagements thereon, said engagements being spaced apart from each other and being positioned at points around said ring, said ring having an inner surface and an outer surface, each of said engagements being positioned on said outer surface, said inner surface engaging the bottle of eye drops, each of said engagements having a bottom end, said bottom end of each of said engagements being open;

a plurality of legs, each of said legs being movably coupled to a respective one of said engagements, each of said legs having a first end and a second end, said first end of each of said legs being inserted into said bottom end of said respective engagement, said second end of each of said legs having a cup being positioned thereon, said cup having an open end, said open end being directed away from said leg upon which said cup is positioned;

a plurality of extensions, each of said extensions being pivotally coupled to a respective one of said legs, each of said extensions being positionable at a selected angle with respect to said respective leg wherein each of said extensions is configured to be aligned with a respective one of a top eyelid and bottom eyelid, each of said extensions spacing said ring away from the eyeball associated with the top and bottom eyelids wherein said ring is configured to align the bottle of eye drops with the eyeball for successfully dispensing eye drops onto the eyeball, each of said extensions having an upper end and a lower end, said upper end of each of said extensions having a coupling ball thereon, said coupling ball on said upper end of each of said extensions being rotatably positioned in said cup on said second end of said respective leg thereby pivotally retaining each of said extensions on said respective leg, each of said extensions being manipulated into the selected angle with respect to said ring to facilitate said ring to be centered around a pupil of the eyeball, each of said extensions comprising a first half slidably engaging a second half such that each of said extensions has a telescopically adjustable length; and a plurality of mounting balls, each of said mounting balls being coupled to a respective one of said extensions wherein each of said mounting balls is configured to engage the conjunctiva sac of a respective one of the top and bottom eyelids, each of said mounting balls being comprised of a smooth material wherein each of said mounting balls is configured to inhibit irritating the conjunctiva sac, each of said mounting balls being comprised of a hypo-allergenic material wherein each of said mounting balls is configured to inhibit initiating an allergic response in the conjunctiva sac, each of said mounting balls being positioned on said lower end of said respective extension.

* * * * *